United States Patent
Landrette et al.

(10) Patent No.: US 10,702,534 B2
(45) Date of Patent: Jul. 7, 2020

(54) COMPOSITIONS AND METHODS RELATING TO THE RADIOPROTECTIVE EFFECTS OF APILIMOD

(71) Applicant: LAM Therapeutics, Inc., Guilford, CT (US)

(72) Inventors: Sean Landrette, Meriden, CT (US); Tian Xu, Guilford, CT (US); Jonathan M. Rothberg, Guilford, CT (US); Henri Lichenstein, Guilford, CT (US)

(73) Assignee: AI Therapeutics, Inc., Guilford, CT (US)

( * ) Notice: Subject to any disclaimer, the term of this patent is extended or adjusted under 35 U.S.C. 154(b) by 0 days.

(21) Appl. No.: 15/938,384

(22) Filed: Mar. 28, 2018

(65) Prior Publication Data

US 2018/0280403 A1    Oct. 4, 2018

Related U.S. Application Data

(60) Provisional application No. 62/479,379, filed on Mar. 31, 2017.

(51) Int. Cl.
| | |
|---|---|
| *A61K 31/5377* | (2006.01) |
| *A61P 39/00* | (2006.01) |
| *A61K 9/00* | (2006.01) |
| *A61K 47/38* | (2006.01) |
| *A61K 45/06* | (2006.01) |

(52) U.S. Cl.
CPC ........ *A61K 31/5377* (2013.01); *A61K 9/0019* (2013.01); *A61K 47/38* (2013.01); *A61P 39/00* (2018.01); *A61K 45/06* (2013.01)

(58) Field of Classification Search
CPC .............................. A61K 31/5377; A61P 39/00
See application file for complete search history.

(56) References Cited

U.S. PATENT DOCUMENTS

| 7,863,270 B2 | 1/2011 | Demko et al. | |
|---|---|---|---|
| 2011/0288081 A1* | 11/2011 | Wada | A61K 31/5377 514/227.8 |

FOREIGN PATENT DOCUMENTS

| CN | 105963300 A | 3/2015 |
|---|---|---|
| WO | WO-2006/128129 A2 | 11/2006 |
| WO | WO-2016/109002 A2 | 7/2016 |

OTHER PUBLICATIONS

Berkey (American Family Physician, 2010, vol. 82, No. 4, pp. 381-388) (Year: 2010).*
Singh et al. Expert Opin. Biol. Ther., 2015, vol. 15, No. 4, pp. 465-471 (Year: 2015).*
Ryu et al. Lab Anim. Res., 2016, vol. 32, No. 2, pp. 116-121 (Year: 2016).*
Burdelya et al. Science, 2008, vol. 320, pp. 226-230 (Year: 2008).*
Plett et al. Health Phys., 2014, vol. 106, No. 1) (Author Manuscript, 20 pages) (Year: 2014).*
Krausz et al. Arthritis & Rheumatism, Jun. 2012, vol. 64, No. 6, pp. 1750-1755 (Year: 2012).*
Heslet, L. et al., (2012). "Acute radiation syndrome (ARS)-treatment of the reduced host defense." *Intl. J. Gen. Med.*, vol. 5:105-115.
Krivokrysenko, V. et al., (Sep. 15, 2015) "The toll-like receptor 5 agonist Entolimod mitigates lethal acute radiation syndrome in non-human primates." *PloS One* pp. 1-30. DOI:10.1371/journal.pone.0135388.
Krivokrysenko, V. et al., (2012). "Identification of granulocyte colony-stimulating factor and interleukin-6 as candidate biomarkers of CBLB502 efficacy as a medical radiation countermeasure" *The J. Pharmacol. Exper. Thera.* vol. 343:497-508.
Neta, R. et al., (1997). "Modulation of radiation damage by cytokines." *Stem Cells*, 15(Supplement 2):87-94.
Wada, Y. et al., (Feb. 2007) "Selective abrogation of Th1 reponse by STA-5326, a potent II-12/IL-23 inhibitor." *Immunobiol.* vol. 109(3):1156-1164.

* cited by examiner

*Primary Examiner* — James D. Anderson
(74) *Attorney, Agent, or Firm* — Muriel Liberto, Esq.; Mintz Levin Cohn Ferris Glovsky and Popeo, P.C.

(57) ABSTRACT

The present disclosure relates to methods for preventing or treating a radiation-induced disease, disorder, or condition by administering apilimod to a subject in need thereof, and related compositions.

19 Claims, 1 Drawing Sheet

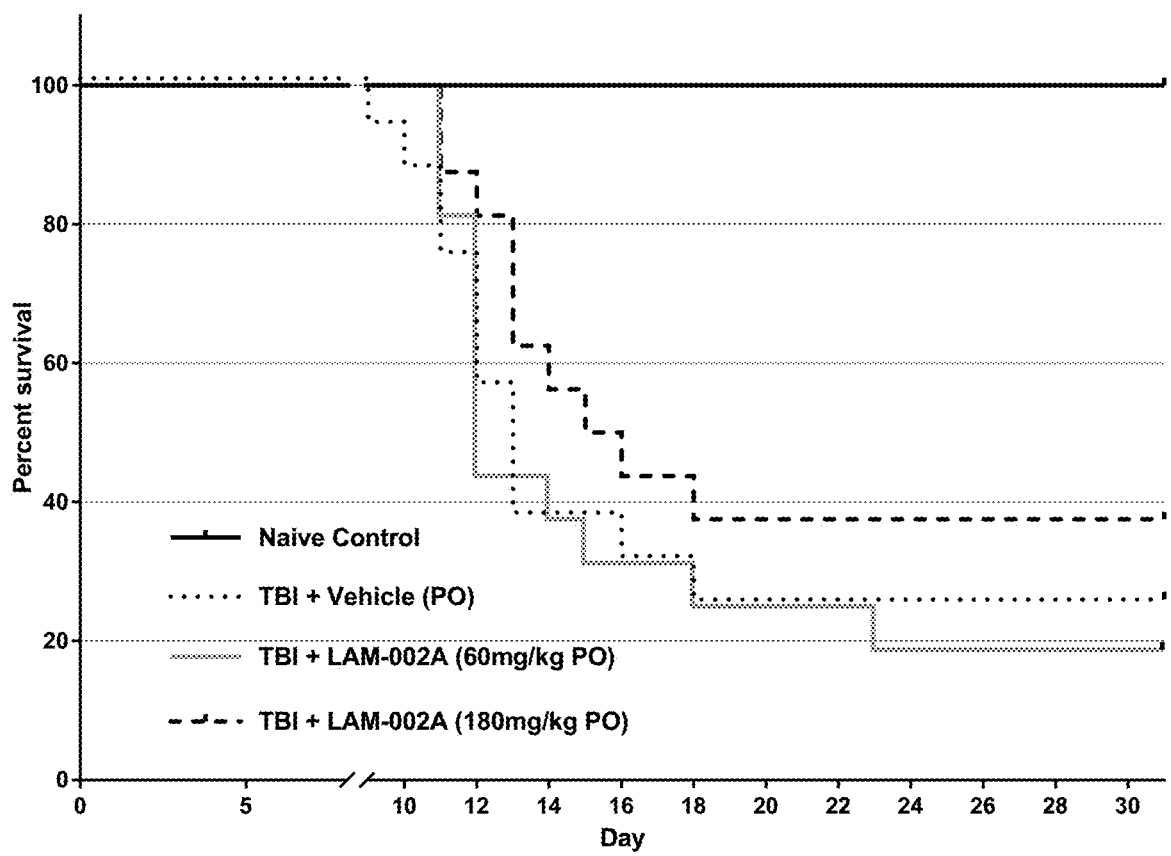

COMPOSITIONS AND METHODS RELATING TO THE RADIOPROTECTIVE EFFECTS OF APILIMOD

CROSS REFERENCE TO RELATED APPLICATIONS

This application is a non-provisional application which claims the benefit of U.S. Provisional Application No. 62/479,379, filed Mar. 31, 2017, which is incorporated herein by reference in its entirety.

FIELD OF THE DISCLOSURE

The present disclosure relates to the use of apilimod in the treatment or prevention of radiation induced diseases, disorders, and conditions.

BACKGROUND OF THE DISCLOSURE

Animal cells and tissues have different radiation sensitivity. In mammals, including humans, the symptoms resulting from exposure to radiation manifest in two phases, an acute phase, which may be referred to as acute radiation disorder, or a late onset phase, which may be referred to as late onset disorder. The acute phase disorder arises from damage to the highly sensitive cells and tissues of the immune system, the gastrointestinal system, and the central nervous system. The clinical symptoms of acute disorder begin with a decrease in lymphocytes followed by, for example, alopecia and skin erythema. The clinical manifestations of chronic disorder may be in the form of increased incidence of certain cancers as well as non-cancer diseases and genetic alterations which appear to occur stochastically rather than being subject to a certain exposure threshold (Kamiya K et al., 2012, Nihon Rinsho 70(3):367-74).

Acute radiation syndrome, also referred to as acute radiation sickness (ARS) is an acute disorder caused by whole body irradiation from a high dose of penetrating radiation (e.g., greater than 1 gray, abbreviated "Gy") during a short time period, typically over a period of minutes. In a human subject receiving high doses of radiation, both mature lymphocytes and bone marrow stem cells were severely damaged, causing profound depletion of granulocytes and natural killer cells, which together defend against microbial (or bacteria and viral) invasion. This damage to the immune system makes exposed subjects particularly vulnerable to death from active infections. In addition, cells responsible for innate immunity were activated and produced inflammatory proteins (Yamaoka M et al., 2004, Radiation Research 161:290-8; Effect of the immune system, Radiation Effect Research Foundation). Filgrastim, an agonist of granulocyte colony-stimulating factor (G-CSF) has been suggested as a treatment for ARS because GCSF can increase white blood cell production thereby possibly enhancing the response of the immune system to microbial infections. However, filgrastim has shown variable positive results in animal studies.

Immune cells are known to be vulnerable to radiation. Radiation triggers the changes and effects in the immune system as well as killing healthy cells after irradiation. Radiation induces apoptosis (programmed cell death) in mature natural killer cells (lymphocytes responsible for innate immunity) as well as T and B lymphoctes (white blood cells responsible for adaptive immunity). Radiation also induces lethal damage to the bone marrow stem cell precursors of monocytes, and granulocytes and natural killer (NK) cells. In individuals receiving high doses of radiation, for example, atomic bomb survivors, both mature lymphocytes and bone marrow stem cells were severely damaged, causing profound depletion of granulocytes and natural killer cells (Park B et al. 2014 Int J Mol Sci 15(1):917-943).

Under certain conditions, radiation treatment can also enhance the immune response. For example, radiation exposure can provide a source of antigen that is well-suited for cross presentation by the host antigen-presenting cells (i.e., dendritic cells) which in turn can induce an antigen-specific immune response during radiotherapy of cancer patients. In addition, other immunopotentiating properties of radiation therapy have been observed, for example its influence on the tumor microenvironment which includes enhancing cell trafficking to tumor sites. At present, the numerous distinct and overlapping cell signaling pathways induced by radiation exposure and their interaction is not entirely understood. But understanding a fuller understanding of these pathways is needed for developing more efficient radiotherapies with beneficial, rather than pathological, biological and immunological consequences (Park B et al. 2014 Int J Mol Sci 15(1):917-943; Eriksson D et al., 2010 Tumor Biol. 31:363-72; Verheij Met al. 2000 Cell Tissue Res 301:133-142).

Several cytokines are believed play a role in innate defenses against ionizing radiation. For example, some studies indicated that mice can be protected from death by administration of interleukin-1 (IL-1), tumor necrosis factor (TNF), stem cell factor (SCF), IL-12, or basic fibroblast growth factor (bFGF), within 18-24 hrs prior to whole body irradiation (Heslet L et al. 2012 Int K Gen Med 5:105-115; Neta R 1997 Stem cells 15:87-94). However, none of these has been developed for use in humans as radioprotective agents.

The Toll-like receptor 5 (TLR5) agonist CBLB502 (entolimod) was granted orphan drug status for reducing the risk of death following a potentially lethal dose of total body irradiation (TBI) when administered during or after exposure to radiation. Entolimod induces nuclear factor NF-κB signaling, activating the innate immune response (Burdelya L et al., 2008 Science 320(5873) 226-230). A single intramuscular injection of entolimod given after a lethal dose of total body irradiation increased survival in tests on non-human primates (NHPs). Entolimod mitigates radiation damage to hematopoietic and gastrointestinal tissues and promotes tissue regeneration. It also accelerates the recovery of peripheral blood cellularity and hemoglobin content, and improves the morphological recovery of hematopoietic and lymphoid organs including bone marrow, thymus, spleen and mesenteric lymph nodes. In addition, treatment with entolimod increased circulating levels of the cytokines G-CSF, IL-6, IL-8 and IL-10 in the peripheral blood. (Krivokrysenko V et al. 2015 PLoS One 10(9): e0135388; Krivokrysenko V et al. 2012 J Pharmacol Exp Ther 343(2)). See also WO 2016/109002.

There remains a need for additional safe and effective therapeutic agents for the treatment and prevention of radiation induced cell and tissue damage and for the treatment and prevention of radiation-induced diseases, disorders, and conditions.

SUMMARY OF THE DISCLOSURE

The disclosure provides compositions and methods related to the use of apilimod in the prophylaxis and treatment of radiation injury. Accordingly, the disclosure provides methods for treating or preventing a radiation-induced disease, disorder, or condition in a subject in need thereof, the method comprising administering an amount of apilimod, or a pharmaceutically acceptable salt thereof, to the subject before, during or after the subject's exposure to a dose of radiation, either alone or in combination with one or more additional therapeutic agents. In embodiments, the radiation is ionizing radiation.

In embodiments, the apilimod is in the form of a dimesylate salt.

In embodiments, the subject in need is a human patient undergoing radiation therapy. In accordance with this embodiment, the dose of radiation is from 60 to 80 gray (Gy) or from 20 to 40 Gy and the dose may be fractionated.

In embodiments, the subject in need is a human subject who has been exposed, or is at risk of imminent exposure to, a dose of whole body irradiation. In accordance with this embodiment, the dose is from 2 to 30 Gy.

In accordance with any of the methods described here, the apilimod may be administered to the subject before or after the subject's exposure to the dose of radiation. In embodiments, the apilimod is administered before the subject's exposure to the dose of radiation. In embodiments, the apilimod is administered between 1 and 24 hours, preferably between 1 and 12 hours or between 1 and 6 hours before the subject's exposure to the dose of radiation. In embodiments, the apilimod is administered after the subject's exposure to the dose of radiation. In embodiments, the apilimod is administered between 1 and 48 hours after the subject's exposure to the dose of radiation, preferably between 1 and 24 hours, between 1 and 12 hours, or between 1 and 6 hours.

In embodiments where the apilimod is administered by an oral or intramuscular route, the effective total daily dose is in the range of 25-500 mg, administered once, twice or three times daily for up to 3 days. In embodiments, the amount is from 0.1-15 mg/kg, or 0.2-12 mg/kg. In embodiments, the total daily dose is in an amount of 25 mg, 50 mg, 100 mg, or 150 mg. In embodiments, the total daily dose is in an amount of 200 mg, 250 mg, 300 mg, 350 mg, 400 mg, 450 mg, or 500 mg. In embodiments, the total daily dose is from about 250 to 500 mg, or from 250 to 400 mg.

In accordance with any of the methods described here, the apilimod may be administered parenterally, by intramuscular injection or intravenous or intra-arterial infusion. In embodiments, the administration is by intramuscular injection in an amount of from 25 to 500 mg.

In accordance with any of the methods described here, the apilimod may be administered orally. In embodiments, oral administration is in an amount of from 25 to 500 mg twice daily, or three times daily for up to 2 days.

In accordance with any of the methods described here, the apilimod may be used in the method as a monotherapy, an adjuvant therapy, or in a combination therapy regimen. In embodiments, the apilimod is used in the method as a monotherapy. In embodiments, the apilimod is used in the method as an adjuvant therapy with a primary therapy comprising one or more additional therapeutic agents. In embodiments, the apilimod is used in a combination therapy regimen with one or more additional therapeutic agents. In embodiments, the one or more additional therapeutic agents is a radioprotective agent selected from the group consisting of a colony stimulating factor, a cytokine, a growth factor, a diluting agent, a blocking agent, a mobilizing agent, a chelating agent, an antioxidant, and a free radical scavenger. In embodiments, the radioprotective agent is selected from granulocyte colony-stimulating factor (G-CSF), including recombinant forms and pegylated derivatives thereof, granulocyte-macrophage colony-stimulating factor (GM-CSF), including recombinant forms thereof, stem cell factor, Flt-3 ligand, keratinocyte growth factor, interleukin-1 fragment IL-1b-rd, and interleukin-12 (IL-12). In embodiments, the one or more additional therapeutic agents further comprises an antibiotic, an antiemetic, an anti-diarrheal, an analgesic, an anxiolytic, and a sedative.

The disclosure also provides a kit comprising apilimod, optionally formulated for parenteral administration, in embodiments optionally formulated for intramuscular injection, the apilimod contained in one or more unit dosage forms of from 25 mg to 250 mg. In embodiments, the unit dosage form is selected from 25 mg, 50 mg, 100 mg, 150 mg, 200 mg, and 250 mg, preferably 25 mg, 50 mg, or 100 mg. In embodiments the unit dosage form is in the form of a vial containing a sterile liquid, a vial containing a lyophilized solid, optionally including a sterile solution for reconstituting the lyophilized solid, or in the form of a preloaded syringe or autoinjector, such as a spring-loaded syringe. In embodiments, the kit further contains other optional elements such as one or more antiseptic solutions or wipes, sterile gloves, gauze pads, bandages, etc. In embodiments, the kit optionally comprises one or more additional radioprotective agents selected from the group consisting of a colony stimulating factor, a cytokine, a growth factor, a diluting agent, a blocking agent, a mobilizing agent, a chelating agent, an antioxidant, and a free radical scavenger.

BRIEF DESCRIPTION OF THE DRAWINGS

FIG. 1: Survival curves of the indicated groups: naïve control (no treatment, no irradiation); total body irradiation (TBI) plus vehicle administered orally (PO, dotted line); TBI plus 60 mg/kg apilimod (PO, light gray line); and TBI plus 180 mg/kg apilimod (PO, dashed line). Statistical significance was determined using the log rank (Mantel-Cox) test.

DETAILED DESCRIPTION OF THE DISCLOSURE

The present invention is based, in part, on the discovery that apilimod is effective to increase the 30 day survival of mice subjected to a lethal dose of ionizing radiation.

The present disclosure provides methods and compositions related to the radioprotective activity of apilimod. In embodiments, the disclosure provides methods relating to the treatment and prevention of radiation-induced injury. In embodiments, the compositions and methods promote the survival of a subject or population of subjects exposed to radiation. In embodiments, the compositions and methods described here promote the recovery of peripheral blood cellularity and hemoglobin content, promote the recovery of bone marrow stem cells, and mitigate radiation damage to the gastrointestinal tract. The compositions and methods described here are applicable both in the context of radiation therapy and in the context of accidental or non-therapeutic radiation exposure, for example as may result from a nuclear accident or detonation of a nuclear weapon. Accordingly, a subject in need of treatment according to the methods described here may be one who is at risk of radiation-induced injury, for example in the context of radiotherapy or in the context of a nuclear accident or from detonation of a nuclear weapon. The subject may also be one who has already been exposed to a dose of ionizing radiation. The dose will differ based on the context of the exposure and may be a whole body exposure or partial, less than whole body exposure.

Radiation absorbed dose in the international system of units (SI system) is measured in the "gray" (Gy). One Gy is the amount of radiation energy absorbed by 1 kilogram of human tissue. In the context of radiation therapy, the dose administered to a typical solid epithelial tumor is in the range of 60 to 80 Gy, while lymphomas are treated with 20 to 40 Gy. Preventive or adjuvant doses are typically relatively lower than the curative dose. For example, about 45-60 Gy for solid epithelial tumors of the breast, head, and neck. In practice, the total dose is often fractionated, meaning it is spread out over time, typically from one to two months for breast, head and neck cancers, e.g., in daily doses five times a week for a total period of five to eight weeks. A typical fractionation schedule for adults may be from 1.8 to 2 Gy per day, five days a week. But typical doses vary significantly by cancer type, from 2.2 Gy/fraction to 20 Gy/fraction. Exemplary fractionation schedules include the Continuous Hyperfractionated Accelerated Radiation therapy (CHART) which was developed for the treatment of lung cancer, and the Accelerated Partial Breast Irradiation (APBI) schedule, used to treat breast cancer. The type of radiation used in radiotherapy is generally X-rays and gamma rays, although other charged particles may be used. A patient may receive an accidental dose of radiation that is much higher than the intended dose, for example on the order of ten times the intended dose. In embodiments, the subject in need of treatment according to the methods described may be a patient undergoing radiation therapy for the treatment of cancer or other disease. In embodiments, apilimod is administered as adjuvant therapy to the radiation treatment. In embodiments, the subject in need of treatment may be a patient accidentally receiving a dose of radiation in excess of the intended dose.

In the context of accidental or non-therapeutic radiation exposure a subject in need of treatment according to the methods described may be a subject suffering from acute radiation syndrome (ARS). In embodiments, the subject was exposed to a high dose of radiation, either partial or whole body irradiation, for example a dose of from about 2-30 Gy. In embodiments, the dose is from 2-5 Gy, from 5-10 Gy, from 10-15 Gy, or from 15-30 Gy. In embodiments, the dose is from 15-20 Gy, from 20-25 Gy, or from 25-30 Gy. In embodiments, the dose is from 2 to 8 Gy or from 2 to 5 Gy.

In embodiments, the radiation is ionizing radiation. In this context, ionizing radiation may be selected from one or more of alpha particles, beta particles, gamma rays, and neutrons. In embodiments, one or more radioactive materials may be the source of the ionizing radiation. For example, the radioactive forms of elements such Americium, Cesium, Cobalt, Uranium, Iodine, Phosphorus, Plutonium, Radium, Strontium, and Tritium.

The disclosure also provides a kit comprising apilimod, optionally formulated for parenteral administration, in embodiments optionally formulated for intramuscular injection, the apilimod contained in one or more unit dosage forms of from 25 mg to 250 mg. In embodiments, the unit dosage form is selected from 25 mg, 50 mg, 100 mg, 150 mg, 200 mg, and 250 mg, for example in the form of a vial containing a sterile liquid, a vial containing a lyophilized solid, optionally including a sterile solution for reconstituting the lyophilized solid, or in the form of a preloaded syringe or autoinjector, such as a spring-loaded syringe. In embodiments, the kit further contains other optional elements such as one or more antiseptic solutions or wipes, sterile gloves, gauze pads, bandages, etc. In embodiments, the kit optionally comprises one or more additional radioprotective agents selected from the group consisting of a colony stimulating factor, a cytokine, a growth factor, a diluting agent, a blocking agent, a mobilizing agent, a chelating agent, an antioxidant, and a free radical scavenger.

Apilimod, also referred to as STA-5326, hereinafter "apilimod", is recognized as a potent transcriptional inhibitor of IL-12 and IL-23 (Wada Y et al. 2007 *Blood* 109: 1156-1164). IL-12 and IL-23 are inflammatory cytokines normally produced by immune cells, such as B-cells and macrophages, in response to antigenic stimulation. Autoimmune disorders and other disorders characterized by chronic inflammation are characterized in part by inappropriate production of these cytokines. Apilimod has potential for use in the treatment of Th1-related autoimmune or immunologic disorders. In immune cells, the selective inhibition of IL-12/IL-23 transcription by apilimod was recently shown to be mediated by apilimod's direct binding to phosphatidylinositol-3-phosphate 5-kinase (PIKfyve) (Cai et al. 2013 *Chemistry and Biol* 20:912-921). PIKfyve plays a role in TLR9 signaling, which is important in innate immunity. Inhibition of PIKyve activity preferentially blocks TLR9 signaling for type I IFN induction in FLT3L-bone marrow-derived DCs (Hayashi K et al. 2015 *Int Immunol* 27(9):435-445).

As used herein, the term "apilimod" refers to the compound of Formula I'':

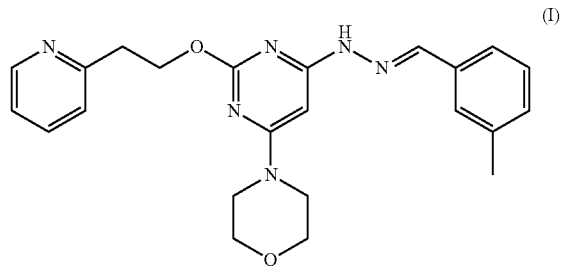 [SMILES: Cc1cccc(/C=N/Nc2cc(N3CCOCC3)nc(OCCc3ccccn3)n2)c1]

The chemical name of apilimod is 2-[2-Pyridin-2-yl)-ethoxy]-4-N'-(3-methyl-benzilidene)-hydrazino]-6-(morpholin-4-yl)-pyrimidine (IUPAC name: (E)-4-(6-(2-(3-methylbenzylidene)hydrazinyl)-2-(2-(pyridin-2-yl)ethoxy) pyrimidin-4-yl)morpholine), and the CAS number is 541550-19-0.

Apilimod can be prepared, for example, according to the methods described in U.S. Pat. Nos. 7,923,557, and 7,863,270, and WO 2006/128129.

In embodiments, apilimod is in the form of a pharmaceutically acceptable salt, preferably a dimesylate salt.

As used herein, the term "pharmaceutically acceptable salt," is a salt formed from, for example, an acid and a basic group of a compound. The acid may be any pharmaceutically acceptable organic or inorganic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid. A pharmaceutically acceptable salt may also generally be prepared from a compound having an acidic functional group, such as a carboxylic acid group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts. In an embodiment, the salt of apilimod comprises methanesulfonate.

The salts described herein can be synthesized from the parent compound by conventional chemical methods such as methods described in Pharmaceutical Salts: Properties, Selection, and Use, P. Hemrich Stahl (Editor), Camille G. Wermuth (Editor), ISBN: 3-90639-026-8, August 2002. Generally, such salts can be prepared by reacting the parent compound with the appropriate acid in water or in an organic solvent, or in a mixture of the two. One salt form can be converted to the free base and optionally to another salt form by methods well known to the skilled person. For example, the free base can be formed by passing the salt solution through a column containing an amine stationary phase (e.g. a Strata-$NH_2$ column). Alternatively, a solution of the salt in water can be treated with sodium bicarbonate to decompose the salt and precipitate out the free base. The free base may then be combined with another acid using routine methods.

In embodiments, apilimod is in the form of a polymorph. As used herein, the term "polymorph" means solid crystalline forms of a compound. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

In embodiments, apilimod is in the form of a hydrate. As used herein, the term "hydrate" refers to a compound, or a salt thereof, which further includes a stoichiometric or non-stoichiometric amount of water bound by non-covalent intermolecular forces.

In embodiments, apilimod is in the form of a clathrate. As used herein, the term "clathrate" means a compound, or a salt thereof, in the form of a crystal lattice that contains spaces (e.g., channels) that have a guest molecule (e.g., a solvent or water) trapped within.

In embodiments, apilimod is in the form of a prodrug. As used herein, the term "prodrug" means a derivative of a compound that can hydrolyze, oxidize, or otherwise react under biological conditions (in vitro or in vivo) to provide the compound. Prodrugs may only become active upon such reaction under biological conditions, or they may have activity in their unreacted forms. Examples of prodrugs contemplated in this disclosure include, but are not limited to, analogs or derivatives of apilimod that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives that comprise —NO, —$NO_2$, —ONO, or —$ONO_2$ moieties. Prodrugs can typically be prepared using well-known methods, such as those described by Burger's *Medicinal Chemistry and Drug Discovery* (1995) 172-178, 949-982 (Manfred E. Wolff ed., 5th ed.).

In embodiments, apilimod is in the form of solvate. As used herein, the term "solvate" or "pharmaceutically acceptable solvate," is a solvate formed from the association of one or more solvent molecules to a molecule of a compound. The term solvate includes hydrates (e.g., hemi-hydrate, monohydrate, dihydrate, trihydrate, tetrahydrate, and the like).

In embodiments, apilimod is in the form of analog. As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

Methods of Treatment

The methods described here are based upon the radioprotective properties of apilimod, as disclosed by the present invention. The methods described here are generally methods for treating or preventing a radiation-induced disease, disorder, or condition in a subject in need thereof. Described are methods in which apilimod is used either as monotherapy, as adjuvant therapy, or in combination therapy for the treatment or prevention of a radiation-induced disease, disorder or condition. The term "monotherapy" refers to the administration of a single active pharmaceutical ingredient ("API") or therapy (which may include non-API based therapies, such as radiotherapy) to a subject in need thereof. Adjuvant therapy refers to the administration of an API or therapy in addition to the primary API or therapy. Adjuvant therapy may be administered either before or after the primary API or therapy. The term "combination therapy" refers to the administration of apilimod along with at least one additional API or therapy as part of a specific treatment regimen intended to provide beneficial effects from the co-action of the therapeutic agents. The beneficial effect of the combination includes, but is not limited to, pharmacokinetic or pharmacodynamic co-action resulting from the combination of APIs and/or therapies. The beneficial effect of the combination may also relate to the mitigation of a toxicity, side effect, or adverse event associated with another API or therapy in the combination. In this context, for example, apilimod may mitigate the damage to normal tissues associated with radiation therapy, or may facilitate the recovery of those tissues.

In embodiments, the disclosure provides a method for the prevention of radiation-induced injury to a subject. In this context, the apilimod is preferably administered between 1 and 72 hours prior to radiation exposure, preferably between 1 and 48 hours, between 1 and 24 hours, between 1 and 12 hours, between 1 and 6 hours, or between 1 and 3 hours. In embodiments, the apilimod is administered about 3 hours before radiation exposure.

In embodiments, the disclosure provides a method for the treatment of radiation-induced injury to a subject. In this context, the apilimod is preferably administered between 1 and 48 hours following the subject's exposure to radiation, preferably between 1 and 24 hours, between 1 and 12 hours, or between 1 and 6 hours.

In the context of the methods described here, administration of apilimod improves the survival and reduces the risk of death in the subject following radiation exposure. In embodiments, administration of apilimod mitigates radiation-induced damage to one or more of the hematopoietic system, gastrointestinal system, and nervous system. In embodiments, apilimod facilitates the recovery of peripheral blood cells following irradiation. In embodiments, apilimod treatment increases the peripheral blood content of one or more of platelets, neutrophils, and hemoglobin. In embodiments, apilimod facilitates the recovery of bone marrow stem cells following irradiation. In embodiments, apilimod limits or reduces radiation-induced damage to the gastrointestinal tract.

In embodiments, the compositions and methods described here may be used in the treatment and prevention of radiation-related disorders, including for example acute radiation syndrome (ARS). In embodiments, treatment with apilimod as described here is effective to reduce mortality or morbidity associated with radiation exposure in a population of subjects. In embodiments, treatment with apilimod as described here is effective to facilitate the recovery of a subject from one or more symptoms of ARS. In embodiments, the one or more symptoms of ARS include redness of the skin, blistering of skin, fibrosis, hair loss, ulceration, and necrosis. In embodiments, the symptoms may include the incidence of wounds and microbial infections. In embodiments, the radiation-related disorder is selected from leukopenia, neutropenia, thrombocytopenia, and anemia.

In the context of methods described here, apilimod may be used as an adjuvant or in combination therapy with any of the following additional agents. In embodiments, an additional agent for use in these methods is selected from one or more of a colony stimulating factor, a cytokine, a growth factor, a diluting agent, a blocking agent, a mobilizing agent, a chelating agent, an antioxidant, and a free radical scavenger. In the context of the methods described here, any of the foregoing may also be referred to as a radioprotective agent or a radioprotectant. Exemplary cytokines and growth factors include granulocyte colony-stimulating factor (G-CSF), pegylated derivatives of G-CSF, recombinant forms of G-CSF such as filgrastim, granulocyte-macrophage colony-stimulating factor (GM-CSF), recombinant forms GM-CSF such as sargramostim, stem cell factor, Flt-3 ligand, keratinocyte growth factor, interleukin-1 fragment IL-1b-rd, and interleukin 12 (IL-12). Exemplary antibiotics include anti-bacterial agents, anti-fungal agents, and anti-viral agents. Exemplary diluting and blocking agents include stable iodide compounds such as those based on potassium iodide. Exemplary mobilizing agents include propylthiouracil and methimazole. Exemplary chelating agents include pentetic acid, also referred to as diethylenetriaminepentaacetic acid (DTPA) and ethylenediaminetetraacetic acid (EDTA), penicillamine, and dimercaprol. Exemplary antioxidants and free radical scavengers include cysteine, cysteamine, glutathione and bilirubin, amifostine (WR-2721), vitamin A, vitamin C, vitamin E, and flavonoids such as Indian holy basil (Ocimum sanctum), orientin and vicenin. Exemplary radioprotectants include the antioxidants and growth factors discussed above as well as genistein, 5-androstenediol, ammonium trichloro (dioxoethylene-O,O')tellurate, thyroid protecting agents, for example the potassium iodide based compounds described above. Additional agents that may be administered in the context of the methods described here include anti-diarrhea agents, antiemetics such as granisetron and ondansetron, analgesics, anxiolytics, sedatives, and antibiotics.

Apilimod may also be used as an adjuvant therapy or in combination therapy with a stem cell transplant or radiation therapy.

In the context of combination therapy, administration of apilimod, or a pharmaceutically acceptable salt, solvate, clathrate, hydrate, polymorph, metabolite, prodrug, analog or derivative thereof, may be simultaneous with or sequential to the administration of the one or more additional APIs or therapies. In another aspect, administration of the different components of a combination therapy may be at different frequencies.

The one or more additional agents can be formulated for co-administration with a compound of the present disclosure in a single dosage form or the one or more additional agents can be administered separately from the dosage form that comprises apilimod. When the additional agent is administered separately from apilimod, it can be by the same or a different route of administration as the compound of the instant disclosure.

Preferably, combination therapy as described herein provides a synergistic response in the subject being treated. In this context, the term "synergistic" refers to the efficacy of the combination being more effective than the additive effects of either single therapy used alone, e.g., as a monotherapy. The synergistic effect of combination therapy according to the disclosure can permit the use of lower dosages and/or less frequent administration of at least one agent in the combination compared to its dose and/or frequency outside of the combination. The synergistic effect can also be manifested in the avoidance or reduction of adverse or unwanted side effects associated with the use of either agent in the combination alone.

In embodiments, apilimod is administered in combination with an agent that mitigates one or more side effects of apilimod selected from any of nausea, vomiting, headache, dizziness, lightheadedness, drowsiness and stress. In one aspect of this embodiment, the additional agent is an antagonist of a subtype of the serotonin receptor, also known as 5-hydroxytryptamine receptors or 5-HT receptors. In one aspect, the additional agent is an antagonist of a 5-HT3 or 5-$HT_{1a}$ receptor. In one aspect, the agent is selected from the group consisting of ondansetron, granisetron, dolasetron and palonosetron. In another aspect, the agent is selected from the group consisting of pindolol and risperidone.

The term "therapeutically effective amount" refers to an amount sufficient to treat, ameliorate a symptom of, reduce the severity of, or reduce the duration of a radiation-induced disease, disorder or condition. The effect can be detected by any assay method known in the art. The precise effective amount for a subject will depend upon the subject's body weight, size, and health; the nature and extent of the condition; and the therapeutic or combination of therapeutics selected for administration. The terms "treatment", "treating" or "treat" describe the management and care of a patient for the purpose of combating a disease, condition, or disorder and include the administration of apilimod or a pharmaceutically acceptable salt, solvate, clathrate, hydrate, polymorph, metabolite, prodrug, analog or derivative thereof, to alleviate the one or more symptoms or complications of exposure to radiation. The terms "prevention", "preventing" or "prevent" describe reducing or eliminating the onset of the symptoms or complications of exposure to radiation. The term "alleviate" is meant to describe a process by which the severity of a sign or symptom of radiation exposure is decreased. A sign or symptom can be alleviated without being eliminated. In an embodiment, the administration of apilimod leads to the elimination of a sign or symptom, however, elimination is not required. Effective dosages are expected to decrease the severity of a sign or symptom.

In accordance with the methods described here, apilimod or a pharmaceutically acceptable salt, solvate, clathrate, hydrate, polymorph, metabolite, prodrug, analog or derivative thereof, can be administered once daily, from two to five times daily, up to two times or up to three times daily, or up to eight times daily. In embodiments, the apilimod is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

An effective amount of apilimod or a pharmaceutically acceptable salt, solvate, clathrate, hydrate, polymorph, metabolite, prodrug, analog or derivative thereof, can range from about 0.1 mg/kg to about 15 mg/kg. In embodiments where the apilimod is administered by an oral or intramuscular route, the effective total daily dose is in the range of 25-500 mg, administered once, twice or three times daily for up to 3 days. Accordingly, a suitable range in mg/kg based on a human of 40 to 150 kg is in an amount between 0.2-12 mg/kg. In embodiments, the total daily dose is in an amount of 25 mg, 50 mg, 100 mg, or 150 mg. In embodiments, the total daily dose is in an amount of 200 mg, 250 mg, 300 mg, 350 mg, 400 mg, 450 mg, or 500 mg. In embodiments, the total daily dose is from about 250 to 500 mg, or from 250 to 400 mg. Effective doses will also vary, as recognized by those skilled in the art, depending on the diseases treated, route of administration, excipient usage, and the possibility of co-usage with other therapeutic treatments such as use of other agents. See, e.g., U.S. Pat. No. 7,863,270, incorporated herein by reference.

In accordance with any of the methods described here, the apilimod may be administered parenterally, by intramuscular injection or intravenous or intra-arterial infusion. In embodiments, the administration is by intramuscular injection in an amount of from 25 to 500 mg per day, administered once, twice, or three times daily.

In accordance with any of the methods described here, the apilimod may be administered orally. In embodiments, oral administration is in an amount of from 25 to 150 mg twice daily, or three times daily for up to 2 days.

In more specific aspects, apilimod or a pharmaceutically acceptable salt, solvate, clathrate, hydrate, polymorph, metabolite, prodrug, analog or derivative thereof is administered at a dosage regimen of 50-250 mg/day up to two times daily for 1, 2, or 3 days.

In embodiments, a "subject in need thereof" is a subject who has been exposed, is likely to be exposed, or is in imminent danger of being exposed, to a dose of radiation, especially ionizing radiation. In embodiments, the subject in need thereof is a patient receiving radiotherapy for cancer or other diseases. A "subject" includes a mammal and can be any mammal, e.g., a human, primate, vertebrate, bird, mouse, rat, fowl, dog, cat, cow, horse, goat, camel, sheep or a pig. Preferably, the mammal is a primate, most preferably a human. The term "patient" refers to a human subject.

Pharmaceutical Compositions and Formulations

The present disclosure provides pharmaceutical compositions comprising an amount of apilimod, or a pharmaceutically acceptable salt, solvate, clathrate, hydrate, polymorph, metabolite, prodrug, analog or derivative thereof, in combination with at least one pharmaceutically acceptable excipient or carrier. A "pharmaceutical composition" is a formulation containing an active pharmaceutical ingredient (API), such as apilimod, in a form suitable for administration to a subject, preferably a human subject. The term "pharmaceutically acceptable" refers to materials which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the disclosure may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present disclosure with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present disclosure may be suspended or dissolved in an oily phase is combined with emulsifying and/or suspending agents. If desired, certain sweetening and/or flavoring and/or coloring agents may be added.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

In embodiments, the apilimod, or a pharmaceutically acceptable salt, solvate, clathrate, hydrate, polymorph, metabolite, prodrug, analog or derivative thereof, is combined with at least one additional active agent or API in a single dosage form. In embodiments, the at least one additional active agent or API is a radioprotective agent, a colony stimulating factor, a cytokine, a growth factor, a diluting agent, a blocking agent, a mobilizing agent, a chelating agent, an antioxidant, and a free radical scavenger. In embodiments, the at least one additional active agent or API may include an anti-diarrhea agent, an antiemetic, an analgesic, an anxiolytic, a sedative, and an antibiotic. In embodiments, the at least one additional active agent or API is selected from ondansetron, granisetron, dolasetron and palonosetron. In embodiments, the at least one additional active agent or API is selected from the group consisting of pindolol and risperidone.

The present disclosure also provides packaging and kits comprising pharmaceutical compositions for use in the methods described here. The kit can comprise one or more containers selected from the group consisting of a bottle, a vial, an ampoule, a blister pack, and a syringe, including a pre-loaded syringe, and an autoinjector such as a spring-loaded syringe. The kit can further include one or more of instructions for use in treating and/or preventing a radiation-induced disease, condition or disorder, one or more applicators, or a sterile solution suitable for reconstituting a pharmaceutical composition comprising apilimod, as described herein. In embodiments, the kit comprises apilimod formulated for parenteral administration, preferably intramuscular injection, and the apilimod is contained in one or more unit dosage forms of 25 mg, 50 mg, or 100 mg, for example in the form of a vial containing a sterile liquid, a vial containing a lyophilized solid, or in the form of a preloaded syringe or autoinjector, as described above. In embodiments, the kit further contains other optional elements such as one or more antiseptic solutions or wipes, sterile gloves, gauze pads, bandages, etc. In embodiments, the kit optionally comprises one or more additional radioprotective agents selected from the group consisting of a colony stimulating factor, a cytokine, a growth factor, a diluting agent, a blocking agent, a mobilizing agent, a chelating agent, an antioxidant, and a free radical scavenger. In embodiments, the kit further comprises one or more additional therapeutic agents selected from an antibiotic, an antiemetic, an anti-diarrheal, an analgesic, an anxiolytic, and a sedative.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

EXAMPLE 1

Prevention of Radiation-Induced Mortality and Weight Loss in Mice

Eighty-six (86) C57B1/6 male mice were randomized into 6 groups. Group 1 (n=6) served as the untreated control group (no apilimod dimesylate or radiation). Animals in Groups 2-6 (n=16/group) were exposed to an 8.5 Gy dose of total body irradiation on Day 0. Radiation was generated with a 160 kilovolt potential (18-ma) source at a focal distance of 25 cm, hardened with a 0.35 mm Al filtration system. Irradiation targeted the total body at a rate of approximately 1.0 Gy/minute. The total radiation dose and dose rate was measured in real time with a Farmer-type ionization chamber and a Fluke 35040 ATD dosimeter. No anesthesia was used during irradiation. Animals were monitored for survival twice daily and those that lost greater than 30% of their total starting body weight were euthanized. Animals in Groups 2 through 6 were dosed with apilimod dimesylate or vehicle exactly 3 hrs prior to radiation on Day 0 via oral gavage (PO) or intraperitoneal injection (IP) as indicated in Table 1 below. All animals were given ad libitum access to acidified drinking (pH 2.8-3.0) water from Day 3 through study completion.

TABLE 1

Study Design

| Group | Number of Animals | Acidified Drinking Water | TBI-Radiation dose | Treatment | Dosing Route/Frequency | Termination |
|---|---|---|---|---|---|---|
| 1 | 6 | pH 2.8-3.0 | — | — | — | Day 31- No Terminal Collections |
| 2 | 16 | Day −3 to 31 | Day 0 (t = 0) 8.5 Gy | Vehicle- 0.5% methylcellulose | PO single dose t = −3 hrs (prior to TBI) | |
| 3 | 16 | | | Apilimod dimesylate 60 mg/kg | | |
| 4 | 16 | | | Apilimod dimesylate 180 mg/kg | | |
| 5 | 16 | | | Vehicle- 0.5% methylcellulose | IP single dose t = −3 hrs (prior to TBI) | |
| 6 | 16 | | | Apilimod dimesylate 60 mg/kg | | |

The results of survival analysis indicate that apilimod dimesylate provides significant survival protection to acutely irradiated mice when delivered by intraperitoneal injection. Both the percentage of surviving animals (6.25 vs. 43.75%) and the median time of survival (13.5 vs. 21 days) were increased by 60 mg/kg administered i.p. There was also a trend towards increased survival when apilimod dimesylate was administered p.o. at 180 mg/kg, but it did not reach statistical significance. Together this data shows that apilimod is radioprotective. In accordance with these results, the effective dose of apilimod dimesylate in a human would be in the range of 150 mg to 500 mg per day, or from 250 mg to 400 mg. In embodiments the dose is in an amount of 150 mg, 200 mg, 250 mg, 300 mg, 350 mg, 400 mg, 450 mg, or 500 mg.

What is claimed is:

1. A method for preventing radiation-induced injury or acute radiation syndrome (ARS) in a subject in need thereof due to the subject's exposure to or expected exposure to a dose of body penetrating radiation equal to 2 or more gray (Gy), the method comprising parenterally administering an amount apilimod, or a pharmaceutically acceptable salt thereof, to the subject before, during or after the subject's exposure to the dose of radiation, either alone or in combination with one or more additional therapeutic agents.

2. The method of claim 1, wherein the radiation is ionizing radiation.

3. The method of claim 1, wherein the subject in need is a human patient undergoing radiation therapy.

4. The method of claim 3, wherein the dose of radiation is from 60 to 80 gray (Gy).

5. The method of claim 4, wherein the dose is fractionated.

6. The method of claim 1, wherein the subject in need is a human subject who has been exposed, or is at risk of imminent exposure to, a dose of whole body irradiation.

7. The method of claim 6, where the dose is from 2 to 30 Gy.

8. The method of claim 1, wherein the apilimod is administered to the subject after the subject's exposure to the dose of radiation.

9. The method of claim 1, wherein the apilimod is administered before the subject's exposure to the dose of radiation.

10. The method of claim 9, wherein the apilimod is administered between 1 and 24 hours before the subject's exposure to the dose of radiation.

11. The method of claim 8, wherein the apilimod is administered between 1 and 48 hours after the subject's exposure to the dose of radiation.

12. The method of claim 1, wherein the apilimod is administered parenterally, by intramuscular injection or intravenous or intra-arterial infusion.

13. The method of claim 1, in which apilimod is used in the method as a monotherapy, an adjuvant therapy, or in a combination therapy regimen.

14. The method of claim 13, wherein the apilimod is used in the method as a monotherapy.

15. The method of claim 13, wherein the apilimod is used in the method as an adjuvant therapy with a primary therapy comprising one or more additional therapeutic agents.

16. The method of claim 13, wherein the apilimod is used in a combination therapy regimen with one or more additional therapeutic agents.

17. The method of claim 15, wherein the one or more additional therapeutic agents is a radioprotective agent selected from the group consisting of a colony stimulating factor, a cytokine, a growth factor, a chelating agent, an antioxidant, and a free radical scavenger.

18. The method of claim 17, wherein the radioprotective agent is selected from granulocyte colony-stimulating factor (G-CSF), granulocyte-macrophage colony-stimulating factor (GM-CSF), stem cell factor, Flt-3 ligand, keratinocyte growth factor, interleukin-1 fragment IL-1b-rd, and interleukin-12 (IL-12).

19. The method of claim 17, wherein the one or more additional therapeutic agents further comprises an antibiotic, an antiemetic, an anti-diarrheal, an analgesic, an anxiolytic, and a sedative.

* * * * *